United States Patent [19]
Gilmore et al.

[11] Patent Number: 5,251,476
[45] Date of Patent: Oct. 12, 1993

[54] METHOD FOR DETERMINING A COEFFICIENT OF MOISTURE EXPANSION OF A WORKPIECE

[75] Inventors: James F. Gilmore, Rochester; Carl A. Lloyd, Bloomfield, both of N.Y.

[73] Assignee: Eastman Kodak Company, Rochester, N.Y.

[21] Appl. No.: 905,586

[22] Filed: Jun. 26, 1992

[51] Int. Cl.$^5$ .................... G01N 25/16; G01N 5/04
[52] U.S. Cl. ............................ 73/73; 177/50; 374/14; 374/55
[58] Field of Search .............. 73/73; 374/6, 55, 14; 177/1, 245, 50

[56] References Cited

U.S. PATENT DOCUMENTS

| | | | |
|---|---|---|---|
| 4,672,842 | 6/1987 | Hasselmann | 374/4 X |
| 4,771,631 | 9/1988 | Lehtikoski et al. | 73/73 |
| 4,923,307 | 5/1990 | Gilmore et al. | |
| 4,924,477 | 5/1990 | Gilmore et al. | |

OTHER PUBLICATIONS

Structural Development and Moisture Absorption Behavior of a Graphite/Epoxy Optical Metering Structure for Landsat-D; R. Cline et al.; pp. 1368-1381.

Moisture and Thermal Expansion of Composite Materials; D. S. Cairns et al.; Nov., 1991; U.S. Dept. of Commerce, NTIS.

*Primary Examiner*—Daniel M. Yasich
*Attorney, Agent, or Firm*—Kevin A. Sembrat

[57] ABSTRACT

A novel method for determining a coefficient of moisture expansion of a single, identified workpiece or coupon. The method includes the steps of positioning the workpiece in a chamber having known environmental parameters; determining a workpiece length change ΔL caused by a chamber induced change in the workpiece moisture content ΔM, by positioning first and second transformers to opposite ends of the single workpiece; and, measuring a chamber induced change in the workpiece moisture content ΔM, by weighing the workpiece.

3 Claims, 3 Drawing Sheets

5,251,476

METHOD FOR DETERMINING A COEFFICIENT OF MOISTURE EXPANSION OF A WORKPIECE

BACKGROUND OF THE INVENTION

This invention relates to a method for precisely determining a coefficient of moisture expansion of a workpiece.

INTRODUCTION TO THE INVENTION

The coefficient of moisture expansion (CME) of a workpiece can provide a measure of a length deformation $\Delta L$ induced in a workpiece by an amount of moisture $\Delta M$ that it may absorb/release. The CME may be expressed by an equation (1):

$$CME = \frac{\Delta L}{L \Delta M} \qquad (1)$$

where, $L$ = length of a workpiece having a uniform thermal strain;

$\Delta L$ = a linear deformation due to a change in moisture; and $\Delta M$ = absorbed/released moisture.

It is important to know the coefficient of moisture expansion, for example, when a workpiece is part of a statically indeterminate system. Here, expansions or contractions $\Delta L$ of the workpiece, induced by a change in moisture $\Delta M$, may be inhibited or entirely prevented in certain directions. This, in turn, may cause significant stresses in the system, which stresses may have to be investigated by way of the coefficient of moisture expansion, and concomitantly accommodated by the system.

SUMMARY OF THE INVENTION

Our motivation for providing a novel method suitable for precisely determining the CME of a workpiece, comes about in the following way.

We are working with workpieces that comprise novel compositions; that may be utilized in systems of exceptional sensitivity and high performance; and, which may be subjected to unusual moisture gradients $\Delta M$. For example, the workpiece may comprise a composite i.e., a non-homogenous graphite/epoxy composite which comprises a critical component of an optics device that is mounted in a spacecraft.

To an end of designing the workpiece to ensure a desired system performance, we determine its coefficient of moisture expansion. The CME's of our workpieces typically define a range of values e.g., from $100.00 \mu$ inch/inch % $M \pm 10.00$ to $300.00 \mu$ inch/inch % $M \pm 10.00$. As indicated therefore, a required precision of the CME computation is approximately $10 \mu$ inch/inch % M.

Attention is now directed to FIG. 1A, which shows one typical and important test facility 10 that may be used in determining the CME of a workpiece. Our strategy in disclosing this typical test facility 10 is three-fold: to make explicit heretofore hidden assumptions about a typical testing methodology; to show that purblindness to these hidden assumptions can vitiate or thwart a desired precision of measurement; and, to help point the way to the novel method of the present invention which makes explicit these hidden assumptions and defines a new high precision CME testing methodology.

Canonical elements of the FIG. 1A test facility 10 include first and second coupons 12, 14 of known length L, and derivatives of a workpiece (not shown) whose CME is to be discerned by way of the coupons 12, 14.

The first coupon 12 is attached at one end to a conventional linear variable differential transformer 16 (LVDT). The LVDT 16 comprises a transformer probe rod or core connected to the coupon 12. In response to moisture expansions/contractions of the coupon 12, the resultant displacements $\Delta L$ of the coupon 12 may be transmitted to the LVDT transformer. This last action, in turn, can convert the displacement $\Delta L$ into a proportional voltage signal, which can be routinely converted into the parameter $\Delta L$ of equation (1), supra.

Canonical elements of the FIG. 1A test facility 10 also include the second coupon 14 connected to a conventional scale 18. The scale 18 can monitor weight gains/losses of the second coupon 14, thereby providing the second required parameter for computation of equation (1), supra, namely, $\Delta M$.

We now make explicit heretofore hidden or not recognized assumptions about the CME methodology realized by way of the FIG. 1A test facility 10. To this end, we also direct attention to FIG. 1B, which comprises our addition to FIG. 1A, and which includes a demarcation of "environmental zones" 20 and 22. In particular, the environmental zone 20 surrounds the first coupon 12, and the environmental zone 22 surrounds the second coupon 14.

Crucial hidden or not recognized assumptions about the FIG. 1 CME methodology include the following points: that the first coupon 12 is absolutely identical with the second coupon 14, and that the coupons 12, 14 share a unique, common testing environment. There is an implicit assumption that the coupons 12, 14 share attributes of "identicality" and "commonality", so that by way of "juxtaposition", two independent measurements $\Delta L$, $\Delta M$, may be inputted to one CME equation, namely, equation (1), supra, thereby determining a precision of measurement.

We now show that the assumptions of identicality and commonality may be untenable, thereby thwarting the obtainment of a required degree of precision.

As to identicality, first recall that the coupons 12, 14 may comprise composite, non-homogenous materials, like graphite/epoxy. We have discovered that the non-homogenity of the coupons 12, 14 can manifest itself several fold, so that the coupons 12, 14 may have a qualitatively different fiber volume, percentage of microcracking, and/or void content. Since these parameters may be directly correlated to a different moisture content, the differences of these parameters from coupon 12 to coupon 14, may directly work to undermine the assumption of identicality. These differences, in turn, can effect an inherent precision of the CME computation.

Moreover, we have discovered that the coupons 12, 14 may define qualitatively different boundary conditions, and have qualitatively different thicknesses, perimeters/lengths, and/or cross-sectional areas. Again, since these last parameters may be directly correlated to a differential moisture content, the difference of these parameters from coupon 12 to coupon 14 may directly work to undermine the assumption of identicality. The loss of identicality, in turn, can effect an inherent precision of the CME computation.

As to commonality, we have discovered that the environmental zones 20 and 22 that are dedicated to each of the two coupons 12, 14 may be qualitatively different. This is because the two environmental zones 20 and 22 may have a different moisture content, or a different temperature, or respond differently to external shocks or perturbations. Since the differences in the two environmental zones 20 and 22 may abrogate the implicit assumption of commonality of environment, a unique basis for combining the independent parameters $\Delta L$, $\Delta M$ into a common CME equation, may be undermined, thereby resulting in a loss of computation precision.

In summary, we have discovered that some important and typical CME methodologies have assumed (or been non-cognizant) of the points of presumed identicality of coupons, and their presumed commonality of testing environment. The consequences of this situation can manifest themselves in a loss of CME precision. As alluded to above, our exposure and critique of the axiomatic assumptions underlying these CME methodologies, helps point the way to the novel method of the present invention, which makes explicit these assumptions and defines a new high precision CME methodology. In particular, we define a novel method for determining a coefficient of moisture expansion of a single, identified workpiece (coupon), comprising the steps of:

(1) positioning said workpiece in a chamber having known environmental parameters;
(2) connecting one end of said workpiece through a core of a first linear variable differential transformer to a weighing means and connecting an opposite end of said workpiece to a core of a second linear variable differential transformer;
(3) measuring changes in said workpiece's length change $\Delta L$ by utilizing said first and second differential transformers caused by a chamber-induced change in said workpiece's moisture content $\Delta M$;
(4) determining said moisture-induced change in said workpiece's moisture content $\Delta M$, by weighing said workpiece utilizing said weighing means; and
(5) utilizing said workpiece's $\Delta L$ and $\Delta M$ values to determine said workpiece's coefficient of moisture expansion.

An important advantage of the novel method is that it can provide computations of the CME equation that have an exceptionally precise magnitude. For example, the CME computations of our workpieces comprising a graphite/epoxy composite may be 100.00 $\mu$ inch/inch % M±10.00, thereby realizing a precision of at least 5 times, for example, 10 times greater than extant CME computation methods.

The inventors realize this significant advantage by exposing the hidden and false assumptions underlying extant methodologies, namely, an employment of two coupons implicitly presumed to be identical and to be tested within a common environment, and jettisoning the two coupon approach in favor of one coupon testing: the one coupon, by definition, obliged to be identical to itself and to be tested in only one environment.

BRIEF DESCRIPTION OF THE DRAWING

The invention is illustrated in the accompanying drawing, in which.

DETAILED DESCRIPTION OF THE INVENTION

Figure 1A:
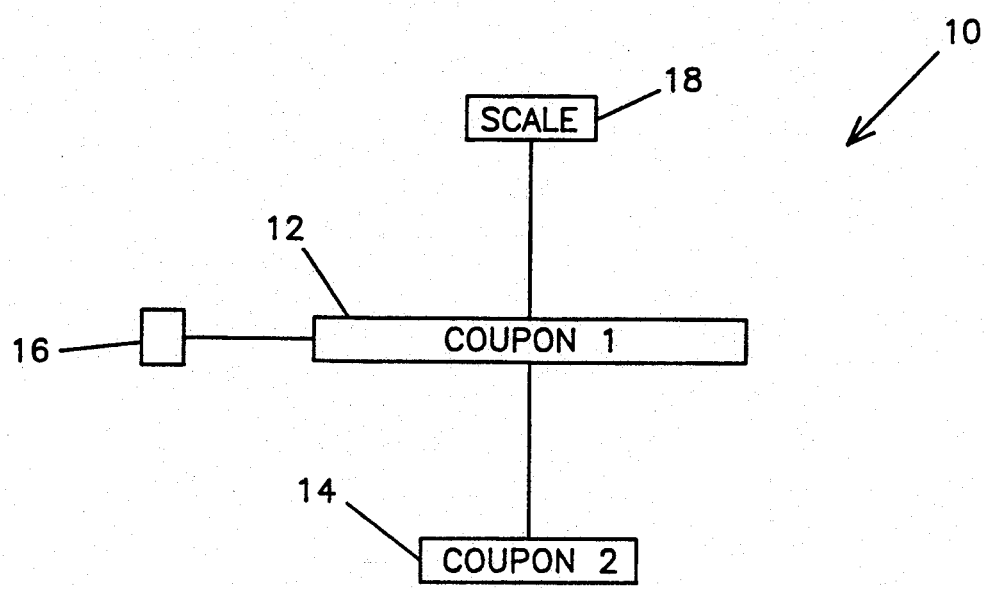
FIG. 1A shows a typical CME test facility.
Figure 1B:
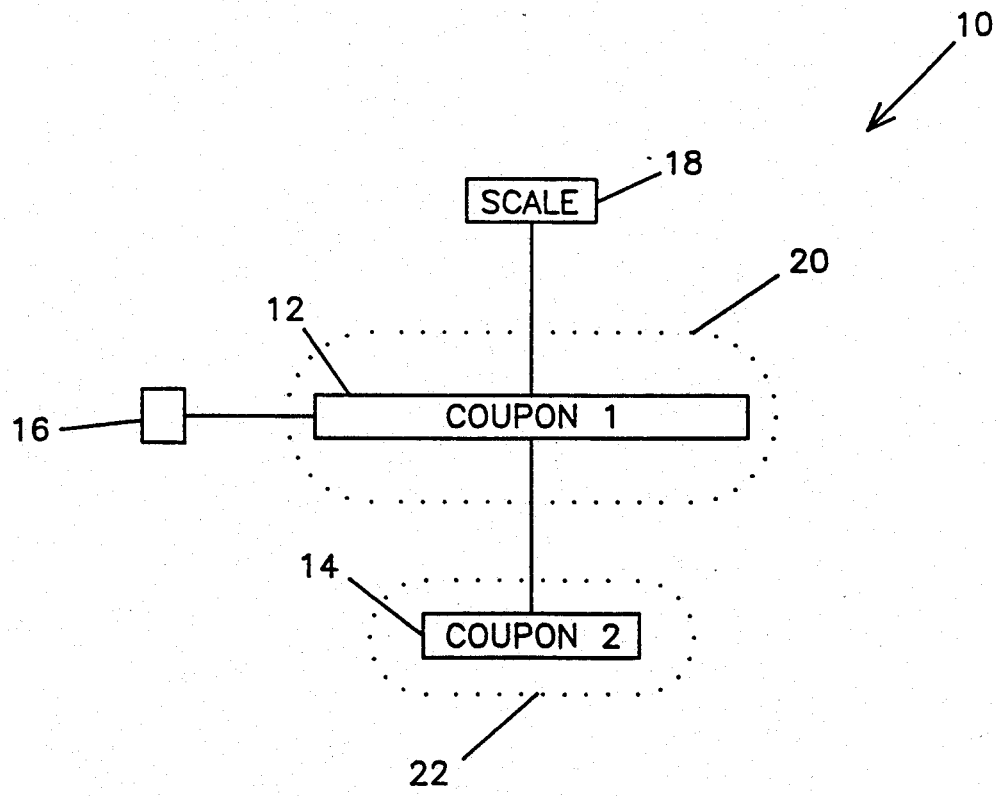
FIG. 1B shows the FIG. 1A CME test facility supplemented by inventor defined environmental zones.
Figure 2A:
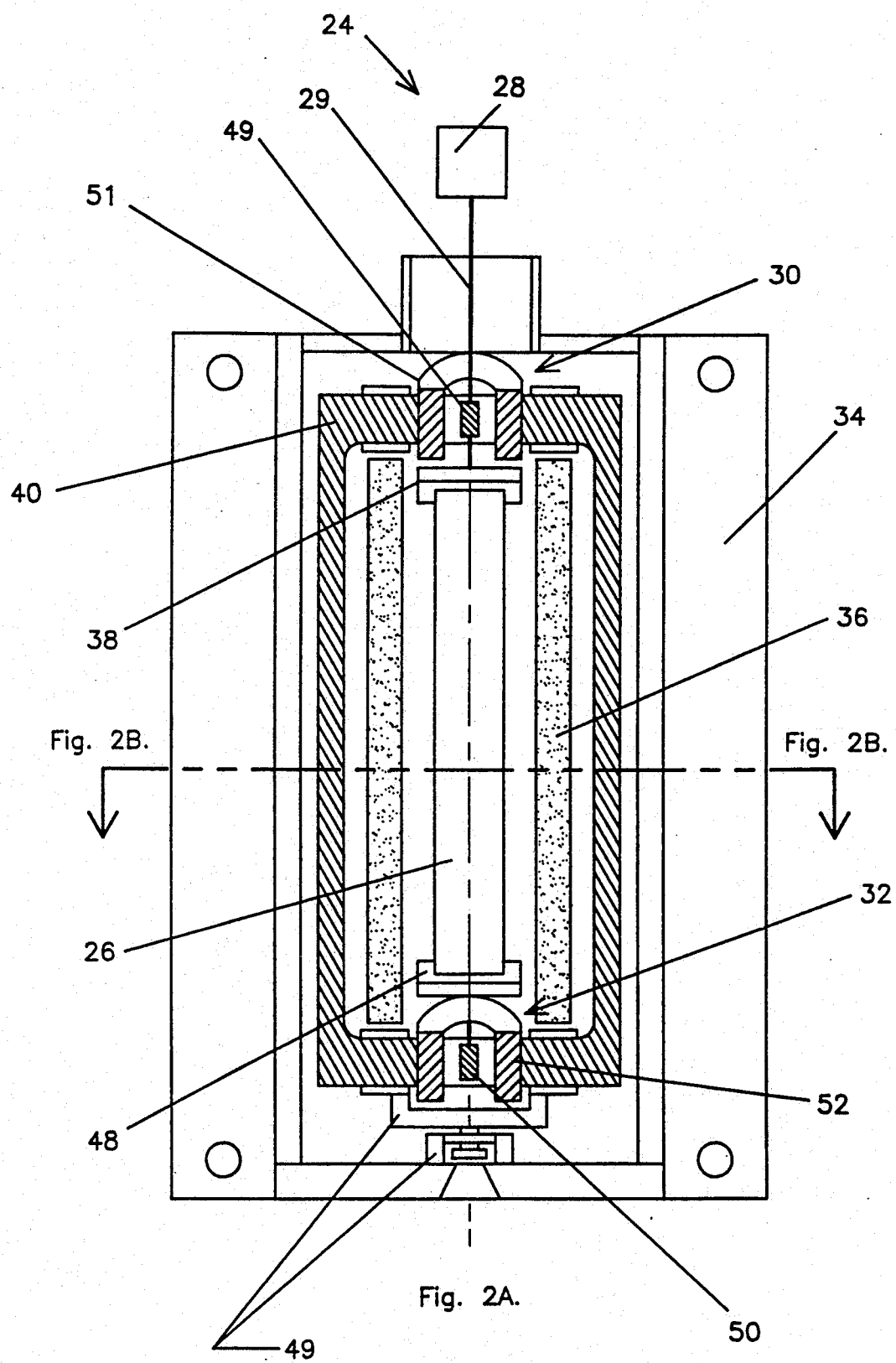
FIGS. 2A and 2B show front and plan cross-sectional views respectively of a CME test facility suitable for realizing a novel CME test method defined by the present invention.
Figure 2B:
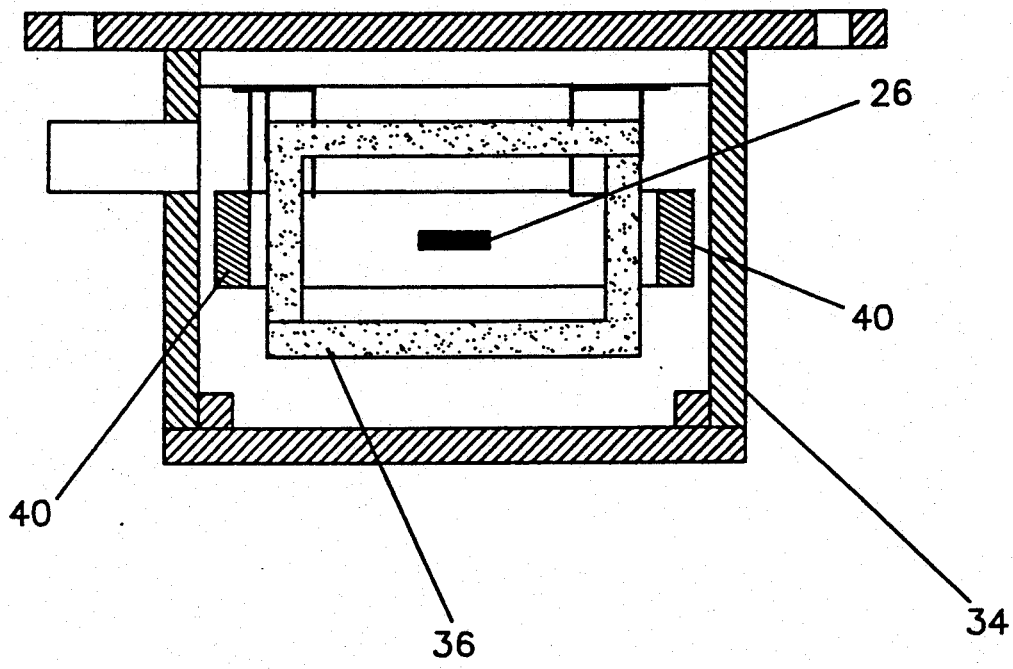

Attention is now directed to FIGS. 2A, and 2B which show front and plan views respectively of a CME test facility 24 suitable for realizing the novel CME method of the present invention.

In overview, the FIGS. 2, 2A and 2B CME test facility 24 suspends one workpiece (coupon) 26 from a high precision scale 28 (not shown) via wire 29, in order to precisely measure the workpiece 26 weight (i.e., $\Delta M$). Preferably, at the same time, two opposing linear variable differential transformers 30, 32 (LVDT) attached to opposite ends of the same workpiece 26, precisely measure its length changes $\Delta L$. Correlation of the data $\Delta M$, $\Delta L$ in one CME equation (CME=$\Delta L/L\Delta M$) may be done without derogation of precision, since the data derive from one workpiece bounded by one environmental zone.

The FIGS. 2A and 2B CME test facility 24 preferably includes a conventional thermal vacuum chamber 34 that can establish and maintain known environmental parameters, for example, temperature, relative humidity, pressure. The chamber 34 preferably comprises aluminum, in order to readily conduct heat and to provide a uniform temperature gradient, and is preferably insulated to help stabilize the chamber 34 temperature. The chamber 34 may alternatively comprise copper, invar or steel. The chamber 34 preferably is positioned on an isolation table, not shown, in order to minimize external pertubations and to provide a stable environment for the workpiece 26.

Preferably included in the chamber 34, and surrounding the workpiece 26, is a conventional high conductivity insulated thermal shroud 36. The thermal shroud 36 can heat and cool the workpiece 26, via external hot and cold water reservoirs, not shown, and can function to provide an optimum heat exchange capability to precisely define the environmental parameters of the workpiece 26.

The thermal shroud 36 may enclose the first and second linear variable differential transformers 30, 32, the latter attached to opposite ends of the workpiece 26, or, as shown in FIG. 2, the LVDT's 30, 32 may preferably be outside the heating shroud 36. The LVDTs' cores (49, 50) are attached to opposing ends of the workpiece 26 via sample support assemblies 38 and 48. The unique sample support assemblies 38 and 48 preferably comprise ball and socket positioners to locate the sides of the workpiece 26, and spring loaded axial positioners to maintain LVDT core and workpiece 26 contact. Further, the LVDT coils (51, 52) are preferably housed in a low conductivity and low coefficient of thermal expansion reference structure 40. In addition, the reference structure contains a preset calibration adjustment screw and brackets 49. The LVDT's 30, 32 function in opposition, so that a required CME parameter $\Delta L$ may be determined in accordance with an equation (2):

$$\Delta L = [(LVDT_{30} + LVDT_{32})_{initial} - (LVDT_{30} + LVDT_{32})_{at\ time\ t}]$$

An important advantage of the employment of opposing LVDT's is that spurious electronic drift and vibration signals may be significantly attenuated.

Preferably, the determination of the CME parameter $\Delta L$ is obtained simultaneously with a determination of the CME parameter $\Delta M$. The last parameter, $\Delta M$, may be obtained via the high precision scale 28 (not shown) that is attached to the workpiece 26 via wire 29.

The parameters $\Delta L$, $\Delta M$ are preferably input to a data acquisition system, for example, a Hewlett Packard Model 86B personal computer, programmed to compute a high precision CME value in accordance with the equation $CME = \Delta L / L \Delta M$.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. A method for determining a coefficient of moisture expansion of a single, identified workpiece, comprising the steps of:
   (1) positioning a workpiece in a chamber having known environmental parameters;
   (2) connecting one end of said workpiece through a core of a first linear variable differential transformer to a weighing means and connecting an opposite end of said workpiece to a core of a second linear variable differential transformer;
   (3) measuring changes in said workpiece's length change, value $\Delta L$, by utilizing said first and second linear variable differential transformers caused by a chamber-induced change in said workpiece's moisture content, value $\Delta M$;
   (4) determining a moisture-induced change in said workpiece's moisture content value $\Delta M$, by weighing said workpiece utilizing said weighing means; and
   (5) utilizing said workpiece's $\Delta L$ and $\Delta M$ values to determine said workpiece's coefficient of moisture expansion.

2. A method according to claim 1, wherein steps (3) and (4) are executed essentially simultaneously.

3. A method according to claim 1, wherein said weighing means comprises a precision scale.

* * * * *